US005627294A

United States Patent [19]
Adams et al.

[11] Patent Number: 5,627,294
[45] Date of Patent: May 6, 1997

[54] MANUFACTURE OF DIHYDROCARBYL DITHIOPHOSPHATES

[75] Inventors: David R. Adams, Faringdon; Patrick F. Ginnelly, Reading, both of United Kingdom

[73] Assignee: Exxon Chemical Patents Inc., Linden, N.J.

[21] Appl. No.: 393,649

[22] Filed: Feb. 24, 1995

[30] Foreign Application Priority Data

Feb. 25, 1994 [GB] United Kingdom ............ 9403604

[51] Int. Cl.$^6$ ............ C07F 9/02; C07F 1/00; C07F 3/00; C07F 5/00
[52] U.S. Cl. ............ 556/13; 556/174; 508/421; 508/369; 508/368; 508/378
[58] Field of Search ............ 556/13, 174; 252/9, 252/34, 35, 36

[56] References Cited

U.S. PATENT DOCUMENTS

| | | | |
|---|---|---|---|
| 3,290,347 | 12/1966 | Miller | 260/429.9 |
| 3,400,106 | 9/1968 | Morita | 260/79.5 |
| 3,691,220 | 9/1972 | Horodysky | 260/429.9 |
| 4,215,067 | 7/1980 | Brannen et al. | 260/429.9 |
| 4,308,154 | 12/1981 | Clason et al. | 252/32.7 E |

FOREIGN PATENT DOCUMENTS

| | | |
|---|---|---|
| 155380 | 10/1974 | Czechoslovakia . |
| 81290 | 2/1983 | Romania . |
| 1105729 | 3/1968 | United Kingdom . |
| 1210059 | 10/1970 | United Kingdom . |
| 2115818 | 9/1983 | United Kingdom . |
| WO84/04319 | 11/1984 | WIPO . |
| WO92/15595 | 9/1992 | WIPO . |

*Primary Examiner*—Porfirio Nazario-Gonzalez
*Attorney, Agent, or Firm*—Kenneth R. Walton; Mary M. Allen

[57] ABSTRACT

An alcohol and/or a carboxylic acid or carboxylate is used to reduce the proportion of sediment obtained in the manufacture of a metal or ammonium dihydrocarbyl dithiophosphate, for example, a zinc dihydrocarbyl dithiophosphate (ZDDP) for use as an antiwear agent/antioxidant in crankcase lubricating oils.

17 Claims, No Drawings

MANUFACTURE OF DIHYDROCARBYL DITHIOPHOSPHATES

The present invention relates to the manufacture of metal or ammonium dihydrocarbyl dithiophosphates, and has particular relevance to the manufacture of metal dihydrocarbyl dithiophosphates, especially zinc dihydrocarbyl dithiophosphates (ZDDPs), for use, for example, in lubricating oil compositions.

Salts of dihydrocarbyl dithiophosphoric acids wherein the individual hydrocarbyl groups contain from 1 to about 30 carbon atoms, especially from 1 to about 18 carbon atoms, typically from 2 to 12 carbon atoms, are widely used in oleaginous compositions, for example, in lubricating oils, including functional fluids, to impart, for example, antiwear and/or antioxidant properties to the compositions. Such salts are commonly prepared by first forming a dihydrocarbyl dithiophosphoric acid, usually by reaction of at least one aliphatic or aromatic alcohol with a phosphorus sulphide, usually $P_2S_5$ (although $P_4S_3$ and other sulphides may be used), and then neutralizing the acid with a metal or ammonium compound, for example, an oxide, hydroxide or carbonate. The product obtained at the end of the neutralization step normally contains sediment, which must be removed, for example, by filtration or centifuging, before the product can be used.

There is a need for a process for the manufacture of dihydrocarbyl dithiophosphates in which the proportion of sediment to be removed at the end of the process is reduced.

The present invention provides the use of an alcohol and/or a carboxylic acid or a salt thereof to reduce the proportion of sediment obtained in the manufacture of a metal or ammonium dihydrocarbyl dithiophosphate. Preferably the alcohol contains at least five carbon atoms. Aliphatic hydrocarbyl alcohols are particularly preferred. The applicants have surprisingly found that the use of the alcohol and/or acid (or salt thereof) in the neutralization step makes it possible to obtain a metal or ammonium salt containing relatively low levels of sediment. Indeed, in some cases the need to remove sediment before the product is used may be completely eliminated.

The invention also provides a process for the manufacture of a metal or ammonium dihydrocarbyl dithiophosphate by reacting a dihydrocarbyl dithiophosphoric acid and a metal compound or an ammonium compound, which process comprises the step of mixing the acid, the metal compound or ammonium compound, and an added hydrocarbyl alcohol containing at least five carbon atoms to form a reaction mixture. In one advantageous embodiment of the invention, the reaction mixture contains a carboxylic acid or a salt thereof as well as the alcohol.

There have been a number of prior proposals for neutralizing dihydrocarbyl dithiophosphoric acids (sometimes referred to hereinafter as DDPAs) in the presence of lower aliphatic alcohols such as ethanol or isopropanol, but none of the documents disclosing such proposals suggests that the presence of an alcohol could lead to a reduction in the proportion of sediment obtained at the end of the neutralization reaction.

British Specification No. 2 115 818 A discloses the use of relatively unreactive solvents, for example, alcoholic solvents such as propanol or butanol, in the neutralization of phosphorodithionic acids derived from vicinal diols.

U.S. Pat. No. 3 691 220 discloses the neutralization of DDPAs to give overbased ZDDPs in the presence of isopropanol and no more than about 2% by weight of water. The use of isopropanol containing at most only a very small proportion of water is said to make it possible to give a product which is more readily purified by filtration.

U.S. Pat. No. 3,400,106, which is referred to in U.S. Pat. No. 3,691,220, is concerned with improved methods for accelerating the vulcanization of rubber by using a basic zinc double salt of an O,O-dialkyl phosphorodithioic acid as an accelerator for a sulphur-containing vulcanizing agent. Methanol, ethanol and isopropanol are disclosed as useful, in admixture with water, as a reaction medium for the reaction of zinc oxide and an O,O-dialkyl phosphorodithioic acid.

Romanian Specification No. 81290 discloses the addition of isobutanol, followed by stirring, to a DDPA which is subsequently purified and reacted with zinc oxide in the presence of acetic acid. The product obtained is filtered.

Czech Specification No. 155 380 discloses the use of an alcohol with 1 to 3 carbon atoms when a DDPA is treated with zinc oxide to give products (which are purified by, for example, centrifuging) having a high zinc content and hence increased thermal stability.

It has been proposed, in U.S. Pat. No. 4,215,067, to reduce haze in ZDDPs by reacting a DDPA with zinc oxide in the presence of a surfactant. It is indicated that the haze, which is caused by particles which cannot be removed by filtration or centrifugation, does not appear to harm engines or processing equipment, but is undesirable in concentrates or single additive packages (presumably because these have an unacceptable appearance). U.S. Pat. No. 4,215,067 is not concerned with reducing the proportion of sediment (that is, material of the type that can be removed by filtration or centrifugation).

There have also been proposals for neutralizing DDPAs in the presence of carboxylic acids or their salts. The documents disclosing such proposals do not indicate, however, that the use of such an acid or salt could lead to a reduction in the proportion of sediment obtained at the end of the neutralization reaction.

British Specification No. 2 053 920 A and the corresponding U.S. Pat. No. 4,308,154, disclose the use of an additional acid when neutralizing DDPAs with a metal base, the products being mixed metal salts containing relatively large proportions of metal and having improved thermal stability.

International Specification No. WO 84/04319, which relates to phosphorus-containing metal salt/olefin compositions and to the reaction products of such compositions with active sulphur, discloses metal salts of mixtures of phosphorus-containing acids and carboxylic acids.

British Specification No. 1 105 729 and U.S. Pat. No. 3,290,347 refer to the use of catalytic amounts of carboxylic acids in the neutralization of DDPAs, the object of the British specification being to obtain products of high thermal stability in high yields and under convenient process conditions, and that of the U.S. patent being to render the neutralization step less erratic as to the proportion of metal compound required and as to the neutralization time. The Romanian specification referred to above also discloses the use of a carboxylic acid, in that case acetic acid, when neutralizing a DDPA.

The dihydrocarbyl dithiophosphates with which the present invention is concerned typically have the formula

wherein M represents a metal atom or an ammonium group;
n represents an integer equal to the valency of M; and
each of $R^1$ and $R^2$, which may be the same or different, represents a hydrocarbyl radical, or $R^1$ and $R^2$ together form a single hydrocarbylene radical, but the invention is not limited to such dihydrocarbyl dithiophosphates. Thus, for example, the dihydrocarbyl dithiophosphates may be basic salts.

When M in the above general formula represents a metal atom, M advantageously represents a Group Ia metal, a Group IIa metal, aluminium, tin, lead, bismuth, molybdenum, titanium, manganese, cobalt, nickel, copper, cadmium, antimony or zinc atom. For some uses, M preferably represents a zinc atom, as in ZDDPs. In other cases, compounds wherein M represents copper may have particular uses. Thus, for example, copper dihydrocarbyl dithiophosphates have proved very useful as, inter alia, antioxidants for lubricating oils.

An ammonium group represented by M may be derived from ammonia or a primary, secondary or tertiary amine. The ammonium group is preferably of the formula $R^3R^4R^5R^6N^+$ wherein $R^3$, $R^4$, $R^5$ and $R^6$ each independently represents hydrogen or a hydrocarbyl group (including a radical derived from a substituted hydrocarbon group, for example, an aminohydrocarbyl, hydroxyhydrocarbyl, or hydroxyhydrocarbyloxyhydrocarbyl radical), or $R^3$ land $R^4$ may together represent a hydrocarbylene group which with the N atom, together form a ring, the hydrocarbylene group optionally, being interrupted by oxygen, sulphur, or other nitrogen atoms. When the groups $R^3$, $R^4$, $R^5$ and/or $R^6$ represent hydrocarbyl groups, these groups are generally hydrocarbyl groups containing up to about 150 carbon atoms and will more often be aliphatic hydrocarbyl groups containing from about 4 to about 30 carbon atoms.

The compounds of the general formula given above contain two hydrocarbyl radicals, which may be the same or different. As used in this specification, the term "hydrocarbyl" denotes a radical having a carbon atom directly attached to the remainder of the molecule and having a hydrocarbon or predominantly hydrocarbon character. Hydrocarbyl radicals include the following:

(1) Hydrocarbon groups; that is, acyclic aliphatic (e.g., alkyl or alkenyl), alicyclic (e.g., cycloalkyl or cycloalkenyl), aromatic, aliphatic- and alicyclic-substituted aromatic, and aromatic-substituted acyclic aliphatic and alicyclic groups, and cyclic groups wherein the ring is completed through another portion of the molecule (that is, any two indicated substituents may together form an alicyclic group). Examples of hydrocarbon groups include methyl, ethyl, octyl, decyl, octadecyl, cyclohexyl, and phenyl groups.

(2) Substituted hydrocarbon groups; that is, groups containing non-hydrocarbon substituents which do not alter the predominantly hydrocarbon character of the group. Examples of suitable substituents include halo, hydroxy, nitro, cyano, alkoxy, and acyl groups.

(3) Hetero groups; that is, groups which, while predominantly hydrocarbon in character, contain atoms other than carbon in a chain or ring otherwise composed of carbon atoms. Suitable hetero atoms include, for example, nitrogen, oxygen and sulphur.

In general, no more than about three substituents or hetero atoms, and preferably no more than one, will be present for each 10 carbon atoms in the hydrocarbyl group.

Especially preferred compounds for use in oil-based compositions are those wherein $R^1$ and $R^2$ in the above general formula contain from 1 to 18, and preferably 2 to 12, carbon atoms. Particularly preferred as $R^1$ and $R^2$ radicals are alkyl radicals having 2 to 8 carbon atoms. Examples of radicals which $R^1$ and $R^2$ may represent are ethyl, n-propyl, i-propyl, n-butyl, i-butyl, sec-butyl, amyl, n-hexyl, 4-methyl-2-pentyl, i-heptyl, i-octyl, i-decyl, dodecyl, octadecyl, 2-ethylhexyl, nonylphenyl, dodecylphenyl, cyclohexyl and methylcyclopentyl radicals.

The total number of carbon atoms in $R^1$ and $R^2$ is preferably sufficient to impart oil-solubility to the compounds. In order to obtain oil solubility, the total number of carbon atoms in $R^1$ and $R^2$ will generally be about 5 or greater.

As indicated earlier, dihydrocarbyl dithiophosphoric acids (DDPAs) may be made by reaction of at least one alcohol, which may be aliphatic or aromatic, with a phosphorus sulphide, which is preferably $P_2S_5$, although $P_4S_3$ and other sulphides may be used where appropriate. Thus, a DDPA of the formula $HSP(S)(OR^1)(OR^2)$, may be made by reacting $P_2S_5$ with $R^1OH$ and $R^2OH$, where $R^1$ and $R^2$ have the meanings given above. (In some cases $R^1$ and $R^2$ will be identical, and in this case a single alcohol is used.)

Any metal compound or ammonium compound which will react with the DDPA may be used in the process of the invention. Advantageously, a metal oxide, hydroxide, carbonate, or basic salt is used. Examples of suitable metal compounds are sodium hydroxide, sodium methoxide, sodium carbonate, potassium hydroxide, potassium carbonate, magnesium oxide, magnesium hydroxide, calcium hydroxide, calcium acetate, zinc oxide, zinc acetate, lead oxide, nickel oxide, and cupric oxide. Suitable ammonium compounds include $R^3NH_2$, $R^3R^4NH$ and $R^3R^4R^5N$, where $R^3$, $R^4$ and $R^5$ have the meanings given above.

The acid(s) and metal or ammonium compounds may be used in stoichiometric proportions to give a neutral dihydrocarbyl dithiophosphate. Alternatively, more than the stoichiometric proportion of the metal compound may be used so that a basic salt is obtained. In one preferred embodiment of the invention, the final product has a zinc to phosphorus mass ratio of greater than 1, advantageously approximately 1.1:1.

In accordance with the invention, the reaction of the DDPA and the metal or ammonium compound may be carried out in the presence of at least one alcohol, which preferably has at least five carbon atoms, especially an aliphatic or aromatic hydrocarbyl alcohol (for example, a phenol), the term "hydrocarbyl" having the meaning given above. Where a mixture of alcohols is used, at least one of the alcohols preferably has at least five carbon atoms. An aliphatic alcohol is preferably acyclic. The alcohol is advantageously oil-soluble, and preferably has 5 to 20 carbon atoms, especially 5 to 12 carbon atoms. Monohydric alcohols may be used, but alcohols with more than one hydroxyl group are not excluded. It may be advantageous in some cases to use an alcohol which is the same as an alcohol, or one of the alcohols, used in forming the DDPA.

An excess of alcohol may if desired be used in the preparation of the DDPA, the DDPA being used in the neutralization step without the separation of the residual alcohol. The alcohol or alcohols used in accordance with the invention to reduce the proportion of sediment, however, is or are mixed with the DDPA after formation of the latter, as the use of a significant excess of alcohol during manufacture of the DDPA would reduce the quality of the DDPA. The term "added alcohol" is used to refer to alcohol added after formation of the DDPA.

Examples of suitable alcohols for use in accordance with the invention are n-pentanol, a sec-butanol/iso-octanol mixture, iso-octanol, nonyl phenol, dinonyl phenol and hexylene glycol. In one advantageous embodiment of the invention, the DDPA is derived from iso-octanol and sec-butanol, and the alcohol is iso-octanol.

The proportion of alcohol required in accordance with the invention may be determined by routine experiment.

Advantageously, at least 1 mass %, and preferably at least 2 mass %, of alcohol is added, based on the weight of the DDPA. Preferably, the molar ratio of added alcohol to the metal compound is at least 0.01:1, and advantageously the said molar ratio is in the range of from 0.01:1 to 1:1, preferably 0.05:1 to 0.75:1. Lower proportions of alcohols than those specified above may be appropriate when a carboxylic acid or a salt thereof is used in addition to the alcohol. If relatively high proportions of alcohol are used, excess alcohol can, if appropriate, be stripped off after completion of the reaction.

As indicated above, the invention also provides the use of at least one carboxylic acid or salt thereof to reduce the proportion of sediment obtained in the manufacture of a metal or ammonium dihydrocarbyl dithiophosphate. The carboxylic acid/salt is advantageously used together with an alcohol as discussed above.

A carboxylic acid used in accordance with the invention is advantageously an aliphatic carboxylic acid, for example, a monocarboxylic acid, preferably an aliphatic carboxylic acid containing 3 to 20 carbon atoms, for example, 3 to 12 carbon atoms. Especially preferred carboxylic acids are those having the formula RCOOH, where R is a linear aliphatic hydrocarbyl radical. Examples of suitable acids are acetic acid, propionic acid, butanoic acid, pentanoic acid, hexanoic acid, decanoic acid, dodecanoic acid and oleic acid. Propionic acid is especially preferred.

Where a salt of a carboxylic acid is used, the salt is preferably the carboxylate of the same metal as is present in the metal dihydrocarbyl dithiophosphate prepared in accordance with this invention. The carboxylic acids from which the salts are derived are desirably the carboxylic acids mentioned above as being advantageous or preferred. Examples of suitable carboxylates include zinc acetate, zinc propionate, and copper acetate.

Mixtures of two or more compounds selected from carboxylic acids and their salts may be used if desired.

The proportion of carboxylic acid/salt to be used may be determined by routine experiment. Advantageously, at least 0.5 mass %, especially at least 3 mass %, of carboxylic acid/salt is used, based on the weight of the DDPA. Preferably, the molar ratio of carboxylic acid/salt to the DDPA is at least 0.1:1, and advantageously the said molar ratio is in the range of from 0.2:1 to 1:1. These proportions of carboxylic acids/salts are appropriate whether or not an alcohol is used in addition to the acid/salt.

A carboxylic acid used in accordance with the invention will react with a basic metal or ammonium compound, as will the DDPA, to give a product containing carboxylic acid and DDPA moieties. The carboxylic acid is normally used in such a proportion that no free carboxylic acid remains at the end of the reaction. A carboxylate, for example, zinc propionate may be used in place of the carboxylic acid, in which case a smaller proportion of the basic metal compound is preferably used.

Some DDPAs will give rise to more sediment on neutralization than others and/or are such that it is relatively difficult to remove the sediment produced. The invention finds particular use in the case of dihydrocarbyl dithiophosphates which give rise to relatively high proportions of sediment and/or which are relatively difficult to purify by filtration or centrigation. For any given DDPA, not every alcohol and/or acid will be equally effective in reducing the proportion of sediment obtained at the end of neutralization, but an effective alcohol and/or acid may be arrived at by routine experiment.

The reaction mixture containing the DDPA and the metal or ammonium compound may also, if required, contain a complexing agent to improve the clarity of the final product. Examples of suitable complexing agents are EDTA, 2-ethylhexenoic acid, and, preferably, acetylacetone. The proportion of complexing agent to be used may be determined by routine experiment. In one case, about 3 wt. % of acetylacetone, based on the weight of DDPA, was found to be appropriate. In some cases, however, a clear product may be obtained without the use of a complexing agent.

Water is formed during the neutralization reaction. In some circumstances, it may be desirable to remove at least part of this water as it is formed, for example, by passing an inert gas such as nitrogen through the reaction mixture. Removal of the water as the reaction proceeds is not, however, always necessary: it may, for example, be sufficient to remove the water after completion of the reaction.

The invention also provides the use of an alcohol, a carboxylic acid or a salt thereof, and a complexing agent to reduce the proportion of sediment obtained in the manufacture of a metal or ammonium dihydrocarbyl dithiophosphate.

The invention further provides a process for the manufacture of a metal or ammonium dihydrocarbyl dithiophosphate which comprises reacting a dihydrocarbyl dithiophosphoric acid with a metal or ammonium compound in the presence of an alcohol, a carboxylic acid or a salt thereof, and a complexing agent. Preferably, water formed by the reaction is at least partially removed during the reaction.

The process of the invention may be carried out under conditions suitable for reacting the DDPA and the metal or ammonium compound in the absence of the alcohol and/or acid used in accordance with the invention. Thus, for example, the reaction may be carried out at a temperature of from about 25° C. to the lowest temperature at which decomposition of a component of the reaction mixture occurs. Preferably, a temperature in the range of from 50° to 200° C. is used, especially 70° to 100° C.

In order to facilitate control of the reaction temperature and mixing of the reactants, the reaction may be carried out in the presence of a substantially inert organic diluent, for example, naphtha, benzene, toluene or, especially, mineral oil. The use of mineral oil has the advantage that it may not be necessary to remove the diluent before the product is used. It may be desirable in some cases, however, to carry out the reaction without a solvent or diluent, giving products which contain only the active ingredient.

The process is preferably carried out by slowly adding the DDPA to a slurry of the metal/ammonium compound, the alcohol and/or acid being in admixture with either the DDPA or the metal/ammonium compound: if desired, the acid, if used, could be added with the DDPA, and the alcohol, if used, could be prior mixed with the metal/ammonium compound, or vice versa. If the reaction mixture is subjected to very intensive mixing, for example using a high shear mixer, it may be possible use lower proportions of alcohol and/or acid than would otherwise be the case. A process for the manufacture of, for example, ZDDPs in which a reaction mixture is subjected to very intensive mixing is described and claimed in International Application No. PCT/EP92/00493 (Publication No. WO 92/15595), the disclosure of which is incorporated herein by reference.

In many cases, dihydrocarbyl dithiophosphates prepared in accordance with the invention contain very low levels of sediment and can be used without filtration or centrifugation to remove sediment. In other cases, the proportion of sediment may be sufficient for removal of sediment by filtration or centrifugation to be necessary, but the proportion of sediment to be removed will be lower than in processes where the additional alcohol/acid is not used. In either case, the invention makes possible a reduction in manufacturing costs and in the safety risks associated with filtration.

As indicated earlier, the invention has particular relevance to the manufacture of metal dihydrocarbyl dithiophosphates, especially ZDDPs, for use in lubricating oil compositions. ZDDPs are widely used as additives for lubricating compositions, functioning primarily as antiwear agents and oxidation inhibitors.

Dihydrocarbyl dithiophosphates manufactured in accordance with the invention for use as lubricating oil additives are oil-soluble or (in common with certain of the other additives referred to below) are dissolvable in oil with the aid of a suitable solvent, or are stably dispersible materials. Oil-soluble, dissolvable, or stably dispersible as that terminology is used herein does not necessarily indicate that the additives are soluble, dissolvable, miscible, or capable of being suspended in oil in all proportions. It does mean, however, that the additives are, for instance, soluble or stably dispersible in oil to an extent sufficient to exert their intended effect in the environment in which the oil is employed. Moreover, the additional incorporation of other additives may also permit incorporation of higher levels of a particular additive, if desired.

Dihydrocarbyl dithiophosphates manufactured in accordance with the present invention can be incorporated into the oil in any convenient way. Thus, they can be added directly to the oil by dispersing or by dissolving them in the oil at the desired level of concentration, typically with the aid of a suitable solvent such, for example, as toluene, cyclohexane, or tetrahydrofuran. Such blending can occur at room temperature or an elevated temperature.

Base oils with which the dihydrocarbyl dithiophosphates may be used include those suitable for use as crankcase lubricating oils for spark-ignited and compression-ignited internal combustion engines, for example, automobile and truck engines, marine and railroad diesel engines, and may be synthetic or natural base oils.

Dihydrocarbyl dithiophosphates manufactured in accordance with the present invention may be employed in a lubricating oil composition which comprises lubricating oil, typically in a major proportion, and the dihydrocarbyl dithiophosphates, typically in a minor proportion. Additional additives may be incorporated in the composition to enable it to meet particular requirements. Examples of aciditives which may be included in lubricating oil compositions are viscosity index improvers, corrosion inhibitors, oxidation inhibitors, friction modifiers, dispersants, detergents, metal rust inhibitors, other anti-wear agents, pour point depressants, and anti-foaming agents.

When lubricating compositions contain one or more of the above-mentioned additives, each additive is typically blended into the base oil in an amount which enables the additive to provide its desired function. Representative effective amounts of such additives, when used in crankcase lubricants, are as follows:

| Additive | Mass % a.i.* (Broad) | Mass % a.i.* (Preferred) |
| --- | --- | --- |
| Viscosity Modifier | 0.01–6 | 0.01–4 |
| Corrosion Inhibitor | 0.01–5 | 0.01–1.5 |
| Oxidation Inhibitor | 0.01–5 | 0.01–1.5 |
| Friction Modifier | 0.01–5 | 0.01–1.5 |
| Dispersant | 0.1–20 | 0.1–8 |
| Detergents/rust inhibitors[+] | 0.01–6 | 0.01–3 |
| Anti-wear Agent | 0.01–6 | 0.01–4 |
| Pour Point Depressant | 0.01–5 | 0.01–1.5 |
| Anti-Foaming Agent | 0.001–3 | 0.001–0.15 |
| Mineral or Synthetic Oil Base | Balance | Balance |

*Mass % active ingredient based on the final oil.
[+]Relatively larger proportions, for example, at least 10 mass % are normally used for marine applications.

When a plurality of additives are employed it may be desirable, although not essential, to prepare one or more additive concentrates comprising the additives (a concentrate sometimes being referred to herein as an additive package) whereby several additives can be added simultaneously to the base oil to form the lubricating oil composition. Dissolution of the additive concentrate(s) into the lubricating oil may be facilitated by solvents and by mixing accompanied with mild heating, but this is not essential. The concentrate(s) or additive package(s) will typically be formulated to contain the additive(s) in proper amounts to provide the desired concentration in the final formulation when the additive package is/are combined with a predetermined amount of base lubricant. Thus, one or more additives manufactured in accordance with the present invention can be added to small amounts of base oil or other compatible solvents along with other desirable additives to form additive packages containing active ingredients in an amount, based on the additive package, of, for example, from about 2.5 to about 90 mass %, and preferably from about 5 to about 75 mass %, and most preferably from about 8 to about 50 mass % by weight, additives in the appropriate proportions with the remainder being base oil.

The final formulations may employ typically about 10 mass % of the additive-package with the remainder being base oil.

The following Examples illustrate the invention.

Proportions of sediment given in the Examples were measured as "initial sediment" and, in some cases, "7-day sediment". In order to obtain the percentage of sediment by volume, a 50 ml sample of the reaction mixture was taken from the hot reaction mixture when the reaction was complete (after stripping of any volatile diluents, alcohols or acids), diluted with 50 ml of heptane, and then centrifuged for 1 hour. The observed volume of sediment (measured, for example, in a calibrated vessel) was multiplied by two in order to obtain the sediment level in the stripped product. This was recorded as the "initial" sediment. The diluted sample was centrifuged again for one hour after standing undisturbed at room temperature for a week, and the sediment level was observed again, being multiplied by two to give the "7-day" sediment. In some cases, the percentage of sediment by mass was also measured: a 50/50 sample as described above was filtered on a 0.1 μm filter, the filter paper being weighed before and after filtering.

COMPARATIVE EXAMPLES 1 TO 3 AND EXAMPLES 1 TO 8

A DDPA prepared by reacting $P_2S_5$ with a stoichiometric proportion of an alcohol mixture comprising 85 mass % sec-butanol and 15 mass % iso-octanol was added slowly to a stirred slurry of zinc oxide in mineral oil or alcohol maintained at 85° C. After addition of all the DDPA, the reaction mixture was maintained at 85° C., with constant stirring for 30 minutes, and the water produced was then removed under vacuum.

In Comparative Examples 1 to 3, no alcohol was present in the reaction mixture. In Examples 1 to 8, the amounts of iso-octanol shown in Table I below were present in the reaction mixture. In Examples 1 to 4, the zinc oxide was slurried in mineral oil, and the iso-octanol was added to the DDPA before the DDPA was added to the slurry. In Examples 5 to 8, the zinc oxide was slurried in the iso-octanol and no mineral oil was used. In Example 1, the reaction mixture was subject to intensive mixing using a high shear mixer. The amounts of zinc oxide, DDPA, and iso-octanol used, and the proportion of sediment obtained (the initial sediment) are shown in Table I. The iso-octanol was added in a sediment-reducing proportion.

400 g of the DDPA used in Examples 1 to 8 was then gradually introduced into the flask at a constant rate over the period shown in the table. Where indicated in Table II, propionic acid (HPr), acetylacetone (AcAc) and/or iso-octanol (ROH) were premixed with the DDPA, and introduced into the flask with the DDPA.

The reaction mixture was maintained at 200° F. (93° C.) for 4 hours, with stirring, following which a sample was removed to determine the initial sediment level. The 7-day sediment level was also determined. The results are shown in Table II.

TABLE I

| Example | Zno Charge (g) | DDPA Charge (g) | $C_8H_{17}OH$ Charge (g) | $C_8$/Zno Ratio (Molar) | Initial Sediment (Volume %) | Initial Sediment (Mass %) |
|---|---|---|---|---|---|---|
| Comp. 1 | 72.2 | 460 | 0 | 0.0 | 0.35 | 0.034 |
| 2 | 72.4 | 450 | 0 | 0.0 | 0.20 | 0.031 |
| 3 | 71.1 | 450 | 0 | 0.0 | 0.40 | 0.033 |
| Ex. 1 | 71.7 | 450 | 6.1 | 0.053 | 0.10 | 0.022 |
| 2 | 72.2 | 450 | 23.0 | 0.200 | 0.20 | 0.014 |
| 3 | 71.1 | 450 | 22.5 | 0.198 | 0.18 | 0.022 |
| 4 | 72.4 | 450 | 22.5 | 0.194 | 0.10 | 0.014 |
| 5 | 71.1 | 450 | 71.1 | 0.626 | 0.06 | 0.015 |
| 6 | 72.4 | 450 | 72.4 | 0.626 | 0.10 | 0.012 |
| 7 | 73.7 | 450 | 73.7 | 0.626 | 0.15 | 0.012 |
| 8 | 71.1 | 450 | 71.1 | 0.626 | 0.10 | 0.007 |

The results obtained in the three groups of Examples, Comparative Examples 1 to 3, Examples 1 to 4, and Examples 5 to 8, were compared. It can be seen that the mean sediment levels for the second and third of these groups were significantly lower than those for the first (comparative) group. The products of Examples 5 to 8 were of sufficient quality to be used without filtration in lubricating oils. The last-mentioned products also had the advantage of being free from diluent oil. Example 1 shows that, with intensive mixing, a significant reduction in sediment levels was obtained even when using a relatively small proportion of iso-octanol.

COMPARATIVE EXAMPLES 4 AND 5 AND EXAMPLES 9 TO 16

65 g zinc oxide, 100 g of diluent oil, and one drop of silicone oil were introduced into a flask equipped with a stirrer, nitrogen sparger, dropping funnel and thermometer. The contents of the flask were stirred and heated to 200° F. (93° C.). Unless indicated to the contrary in Table II below, nitrogen was passed through the mixture at 1 liter/minute.

TABLE II

| Example | DDPA rate (hrs) | HPr Charge (g) | AcAc Charge (g) | ROH Charge (g) | Initial Sediment (vol %) | 7-day Sediment (vol %) |
|---|---|---|---|---|---|---|
| Comp 4 | 1.5 | — | — | — | 0.32 | 0.32 |
| 5 | 1.5 | — | 12 | — | 0.40 | 0.40 |
| EX. 9 | 1.5 | 15 | — | — | 0.09 | 0.18 |
| 10* | 1.5 | 15 | 12 | — | 0.04 | 0.20 |
| 11 | 1.0 | 15 | 12 | — | 0.02 | 0.06 |
| 12 | 2.0 | 8 | 12 | — | 0.12 | 0.20 |
| 13 | 2.0 | 15 | 12 | — | 0.04 | 0.10 |
| 14 | 1.0 | 15 | 12 | 10 | 0.02 | 0.03 |
| 15 | 2.0 | 8 | 12 | 5 | 0.06 | 0.18 |
| 16 | 2.0 | 15 | 12 | 10 | 0.01 | 0.02 |

*No nitrogen sparge

It can be seen that, while the use of cetylacetone alone results in an increase in sediment levels, the use of propionic acid and acetylacetone leads to a reduction in sediment levels. A further reduction is obtained when iso-octanol is also used. When the iso-octanol was replaced by a 85:15 by mass mixture of sec-butanol and iso-octanol, sediment was still reduced, but to a lesser extent, apparently because at least some of the more volatile sec-butanol was driven out of the reaction mixture before the reaction was complete.

We claim:

1. A process for the manufacture of a metal or ammonium dihydrocarbyl dithiophosphate by reacting a dihydrocarbyl dithiophosphoric acid and a metal compound or an ammonium compound, which process comprises the step of mixing the acid, the metal compound or ammonium compound, and an added hydrocarbyl alcohol containing at least five carbon atoms to form a reaction mixture.

2. A process as claimed in claim 1, wherein water formed by the reaction is at least partially removed during the reaction.

3. A process as claimed in claim 1, wherein the reaction mixture also contains a carboxylic acid or a salt thereof.

4. A process as claimed in claim 1, wherein the carboxylic acid or the salt thereof has 3 to 20 carbon atoms.

5. A process as claimed in any one of claim 4, wherein the carboxylic acid or the salt thereof contains not more than 12 carbon atoms.

6. A process as claimed in claim 5, where the carboxylic acid is propionic acid.

7. A process as claimed in claim 1, wherein the reaction mixture also contains a complexing agent.

8. A process as claimed in claim 1, wherein the complexing agent is acetylacetone.

9. A process as claimed in claim 1, wherein the metal is selected from Group Ia metals, Group IIa metals, aluminum, tin, lead, bismuth, molybdenum, manganese, cobalt, nickel, copper, cadmium, antimony, and zinc.

10. A process as claimed in claim 1, wherein the metal is zinc.

11. The process as claimed in claim 10, wherein the mass ratio of zinc to phosphorus in the dithiophosphate is greater than 1.

12. A process as claimed in claim 10, wherein the dihydrocarbyl dithiophosphoric acid is derived from iso-octanol and sec-butanol, and wherein the alcohol is iso-octanol.

13. A process as claimed in claim 1, wherein at least 1 mass % of the alcohol is added to form the reaction mixture, based on the weight of the dihydrocarbyl dithiophosphoric acid.

14. A process as claimed in claim 1, wherein the molar ratio of the added alcohol to the metal or ammonium compound is at least 0.01:1.

15. A process as claimed in claim 14, wherein the said molar ratio is in the range of from 0.01:1 to 1:1.

16. A process for the manufacture of a metal or ammonium dihydrocarbyl dithiophosphate which comprises reacting a dihydrocarbyl dithiophosphate acid with a metal compound or ammonium compound in the presence of an alcohol, a carboxylic acid or a salt thereof, and a complexing agent.

17. A process as claimed in claim 16, wherein water formed by the reaction is at least partially removed during the reaction.

* * * * *